(12) United States Patent
Trotter et al.

(10) Patent No.: US 7,723,352 B2
(45) Date of Patent: May 25, 2010

(54) ISOQUINOLINONE POTASSIUM CHANNEL INHIBITORS

(75) Inventors: B. Wesley Trotter, Glenside, PA (US); Christopher Claiborne, Cambridge, MA (US); Gerald S. Ponticello, Lansdale, NJ (US); Charles J. McIntyre, Lansdale, PA (US); Nigel Liverton, Harleysville, PA (US); David A. Claremon, Maple Glen, PA (US)

(73) Assignee: Merck Sharp & Dohme, Rahway, NJ (US)

( * ) Notice: Subject to any disclaimer, the term of this patent is extended or adjusted under 35 U.S.C. 154(b) by 1044 days.

(21) Appl. No.: 10/571,870

(22) PCT Filed: Sep. 17, 2004

(86) PCT No.: PCT/US2004/030431

§ 371 (c)(1),
(2), (4) Date: Mar. 15, 2006

(87) PCT Pub. No.: WO2005/030791

PCT Pub. Date: Apr. 7, 2005

(65) Prior Publication Data

US 2007/0027177 A1 Feb. 1, 2007

Related U.S. Application Data

(60) Provisional application No. 60/505,101, filed on Sep. 23, 2003.

(51) Int. Cl.
C07D 471/02 (2006.01)
A61K 31/47 (2006.01)

(52) U.S. Cl. .......................................... 514/292; 546/94
(58) Field of Classification Search ........................ None
See application file for complete search history.

(56) References Cited

U.S. PATENT DOCUMENTS

| | | | |
|---|---|---|---|
| 3,594,380 A | 7/1971 | Sulkowski | |
| 3,878,215 A | 4/1975 | Houlihan et al. | |
| 4,897,391 A | 1/1990 | Friary | |
| 5,482,967 A | 1/1996 | Natsugari et al. | |

FOREIGN PATENT DOCUMENTS

EP    1 396 488 A1    3/2004

WO    WO 96/36611    11/1996
WO    WO 02/24655    3/2002

OTHER PUBLICATIONS

Couture, Axel et al., Tetrahedron, vol. 52, No. 12, pp. 4433-4448 (1996).
Chemical Abstracts Service No. XP002486887, Database Accession No. 2000:101888.
Chemical Abstracts Service No. XP002486888, Database Accession No. 1987:575850.
CrossFire Beilstein Database XP-002486889, Database Accession No. 191948.
CrossFire Beilstein Database XP-002486890, Database Accession No. 3561620.
Chemical Abstracts Service No. XP002486891, Database Accession No. 1995:699369.
Chemical Abstracts Service No. XP002486892, Database Accession No. 1988:493386.
Chemical Abstracts Service No. XP002486893, Database Accession No. 1999:206731.
Chemical Abstracts Service No. XP002486894, Database Accession No. 1989:23703.
Chemical Abstracts Service No. XP002486887, Database Accession No. 2000:101888, 2000.
Chemical Abstracts Service No. XP002486888, Database Accession No. 1987:575850, 1987.
Chemical Abstracts Service No. XP002486891, Database Accession No. 1995:699369, 1995.
Chemical Abstracts Service No. XP002486892, Database Accession No. 1988:493386, 1998.
Chemical Abstracts Service No. XP002486893, Database Accession No. 1999:206731, 1999.
Chemical Abstracts Service No. XP002486894, Database Accession No. 1989:23703, 1989.

*Primary Examiner*—Zinna N Davis
(74) *Attorney, Agent, or Firm*—Heidi M. Struse; Richard S. Parr; Mark R. Daniel

(57) ABSTRACT

The present invention relates to compounds having the structure (I) useful as potassium channel inhibitors to treat cardiac arrhythmias, and the like.

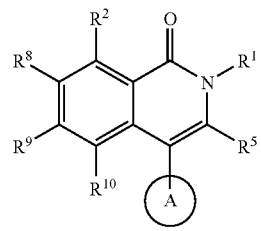

8 Claims, No Drawings

ISOQUINOLINONE POTASSIUM CHANNEL INHIBITORS

CROSS REFERENCE TO RELATED APPLICATION

This application is a U.S. National Phase application under 35 U.S.C. 371 of PCT Application No. PCT/US2004/030431, filed Sep. 17, 2004, which claims priority under 35U.S.C. 119(e) from U.S. Provisional Application Ser. No. 60/505,101, filed Sep. 23, 2003.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like.

Atrial fibrillation (AF) is the most common sustained cardiac arrhythmia in clinical practice and is likely to increase in prevalence with the aging of the population. While AF is rarely fatal, it can impair cardiac function and lead to complications such as the development of congestive heart failure, thromboembolism, or ventricular fibrillation.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation,* 102:2665-2670), but pose an unacceptable risk of potentially lethal ventricular proarrhythmia and thus may increase mortality (Pratt, C M, Moye, L A, *Am J. Cardiol.,* 65:20B-29B, 1990; Waldo et al, *Lancet,* 348:7-12, 1996; Torp-Pedersen et al, *Expert Opin. Invest. Drugs,* 9:2695-2704, 2000). These observations demonstrate a clear unmet medical need to develop safer and more efficacious drugs for the treatment of atrial arrhythmias. Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation,* 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs,* 9:2695-2704, 2000). However, these agents have the major liability of an enhanced risk of proarrhythmia at slow heart rates.

The ultrarapid delayed rectifier $K^+$ current, $I_{Kur}$, has been observed specifically in human atrium and not in ventricle. The molecular correlate of $I_{Kur}$ in the human atrium is the potassium channel designated Kv1.5. $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic after depolarizations and acquired long QT syndrome observed during treatment with current Class III drugs. Kv1.5 blockers exhibiting these properties have been described (Peukert et al, *J. Med. Chem.,* 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

This invention relates to potassium channel inhibitors of general structural Formula I

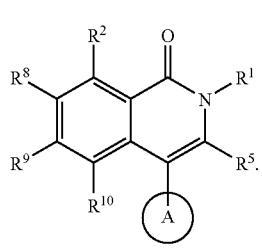

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The present invention is a compound of formula I

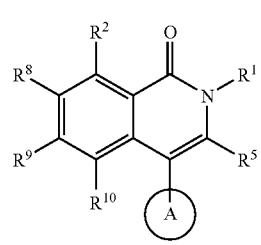

or a pharmaceutically acceptable salt, crystal form, or hydrate, wherein:

A is
  a) an aryl ring, wherein any stable aryl ring atom is independently unsubstituted or substituted with
    1) halogen,
    2) $NO_2$,
    3) CN,
    4) $CR^{46}=C(R^{47}R^{48})_2$,
    5) $C\equiv CR^{46}$,
    6) $(CR^iR^j)_rOR^{46}$,
    7) $(CR^iR^j)_rN(R^{46}R^{47})$,
    8) $(CR^iR^j)_rC(O)R^{46}$,
    9) $(CR^iR^j)_rC(O)OR^{46}$,
    10) $(CR^iR^j)_rR^{46}$,
    11) $(CR^iR^j)_rS(O)_{0-2}R^{61}$,
    12) $(CR^iR^j)_rS(O)_{0-2}N(R^{46}R^{47})$,
    13) $OS(O)_{0-2}R^{61}$,
    14) $N(R^{46})C(O)R^{47}$, 15) $N(R^{46})S(O)_{0-2}R^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo, or b) a heteroaryl ring selected from the group consisting of
   a 5-membered unsaturated monocyclic ring with 1, 2, 3 or 4 heteroatom ring atoms selected from the group consisting or N, O or S,
   a 6-membered unsaturated monocyclic ring with 1, 2, 3 or 4 heteroatom ring atoms selected from the group consisting N, O and S, and
   a 9- or 10-membered unsaturated bicyclic ring with 1, 2, 3 or 4 heteroatom ring atoms selected from the group consisting or N, O or S;
   wherein any stable S heteroaryl ring atom is unsubstituted or mono- or di-substituted with oxo, and any stable C or N heteroaryl ring atom is independently unsubstituted or substituted with
   1) halogen,
   2) $NO_2$,
   3) CN,
   4) $CR^{46}=C(R^{47}R^{48})_2$,
   5) $C\equiv CR^{46}$,
   6) $(CR^iR^j)_rOR^{46}$,
   7) $(CR^iR^j)_rN(R^{46}R^{47})$,
   8) $(CR^iR^j)_rC(O)R^{46}$,
   9) $(CR^iR^j)_rC(O)OR^{46}$,
   10) $(CR^iR^j)_rR^{46}$,
   11) $(CR^iR^j)_rS(O)_{0-2}R^{61}$,
   12) $(CR^iR^j)_rS(O)_{0-2}N(R^{46}R^{47})$,
   13) $OS(O)_{0-2}R^{61}$,
   14) $N(R^{46})C(O)R^{47}$,
   15) $N(R^{46})S(O)_{0-2}R^{61}$,
   16) $(CR^iR^j)_rN(R^{46})R^{61}$,
   17) $(CR^iR^j)_rN(R^{46})R^{61}OR^{47}$,
   18) $(CR^iR^j)_rN(R^{46})(CR^kR^l)_sC(O)N(R^{47}R^{48})$,
   19) $N(R^{46})(CR^iR^j)_rR^{61}$,
   20) $N(R^{46})(CR^iR^j)_rN(R^{47}R^{48})$,
   21) $(CR^iR^j)_rC(O)N(R^{47}R^{48})$, or
   22) oxo;

$R^1$ is selected from the group consisting of
1) hydrogen,
2) $(CR^aR^b)_nR^{40}$,
3) $(CR^aR^b)_nOR^{40}$,
4) $(CR^aR^b)_nN(R^{40}R^{41})$,
5) $(CR^aR^b)_nN(R^{40})C(O)OR^{41}$,
6) $(CR^aR^b)_nN(R^{40})(CR^cR^d)_2N(R^{41})C(O)R^{49}$,
7) $C_{3-8}$ cycloalkyl,
8) $(CR^aR^b)_nC(O)OR^{40}$,
9) $(CR^aR^b)_nN(R^{40})(CR^cR^d)_{1-3}R^{41}$,
10) $(CR^aR^b)_nS(O)_{0-2}R^6$,
11) $(CR^aR^b)_nS(O)_{0-2}N(R^{40}R^{41})$,
12) $(CR^aR^b)_nN(R^{40})R^6OR^{41}$,
13) $(CR^aR^b)_nN(R^{40})(CR^cR^d)_{0-6}C(O)N(R^{41}R^{42})$;

$R^5$ is selected from the group consisting of
1) hydrogen,
2) halogen,
3) $S(O)_{0-2}N(R^{53}R^{50})$,
4) $S(O)_{0-2}R^{62}$,
5) $CH_3$,
6) $C_3$-$C_6$ alkyl,
7) $C_3$-$C_{10}$ cycloalkyl,
8) $R^{82}$, said alkyl, and cycloalkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$;

or $R^1$ and $R^5$ together with the atoms to which they are attached, form a ring selected from the group of structures consisting of

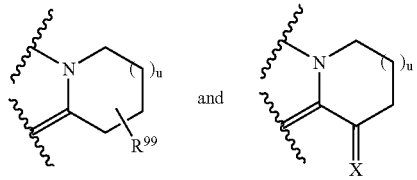

where u is 0 or 1, $R^{99}$ is hydrogen or —OH, and X is O or =NOH;

$R^2$, $R^8$, $R^9$ and $R^{10}$ are independently selected from:
1) hydrogen,
2) halogen,
3) $NO_2$,
4) CN,
5) $CR^{43}=C(R^{44}R^{45})$,
6) $C\equiv CR^{43}$,
7) $(CR^eR^f)_pOR^{43}$,
8) $(CR^eR^f)_pN(R^{43}R^{44})$,
9) $(CR^eR^f)_pC(O)R^{43}$,
10) $(CR^eR^f)_pC(O)OR^{43}$,
11) $(CR^eR^f)_pR^{43}$,
12) $(CR^eR^f)_pS(O)_{0-2}R^{60}$,
13) $(CR^eR^f)_pS(O)_{0-2}N(R^{43}R^{44})$,
14) $OS(O)_{0-2}R^{60}$,
15) $N(R^{43})C(O)R^{44}$,
16) $N(R^{43})S(O)_{0-2}R^{60}$,
17) $(CR^eR^f)_pN(R^{43})R^{60}$,
18) $(CR^eR^f)_pN(R^{43})R^{60}OR^{44}$,
19) $(CR^eR^f)_pN(R^{43})(CR^gR^h)_qC(O)N(R^{44}R^{45})$,
20) $N(R^{43})(CR^eR^f)_pR^{60}$,
21) $N(R^{43})(CR^eR^f)_pN(R^{44}R^{45})$, and
22) $(CR^eR^f)_pC(O)N(R^{43}R^{44})$, or $R^2$ and $R^8$ are independently as defined above, and $R^9$ and $R^{10}$, together with the atoms to which they are attached, form the ring

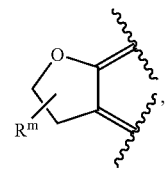

where $R^m$ is $C_{1-6}$alkyl;

$R^a$, $R^b$, $R^c$, $R^d$, $R^e$, $R^f$, $R^g$, $R^h$, $R^i$, $R^j$, $R^k$, and $R^l$ are independently selected from the group consisting of:
1) hydrogen,
2) $C_1$-$C_6$ alkyl,
3) halogen,
4) aryl,
5) $R^{80}$,
6) $C_3$-$C_{10}$ cycloalkyl, and
7) $OR^4$, said alkyl, aryl, and cycloalkyl being unsubstituted, monosubstituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$ and $R^{17}$;

$R^4$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{53}$ and are independently selected from the group consisting of
1) hydrogen,
2) $C_1$-$C_6$ alkyl,
3) $C_3$-$C_{10}$ cycloalkyl,
4) aryl,
5) $R^{81}$,
6) $CF_3$,
7) $C_2$-$C_6$ alkenyl, and
8) $C_2$-$C_6$ alkynyl,
said alkyl, aryl, and cycloalkyl is unsubstituted, monosubstituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;

$R^6$, $R^{60}$, $R^{61}$, $R^{62}$ and $R^{63}$ are independently selected from the group consisting of
1) $C_1$-$C_6$ alkyl,
2) aryl,
3) $R^{83}$, and
4) $C_3$-$C_{10}$ cycloalkyl;
said alkyl, aryl, and cycloalkyl is unsubstituted, monosubstituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, and $R^{29}$ are independently selected from the group consisting of
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$,
10) $C(O)R^{51}$,
11) CN,
12) $C(O)N(R^{51}R^{52})$,
13) $N(R^{51})C(O)R^{52}$,
14) $S(O)_{0-2}R^{63}$,
15) $NO_2$, and
16) $N(R^{51}R^{52})$;

$R^{80}$, $R^{81}$, $R^{82}$, $R^{83}$ and $R^{84}$ are independently selected from a group of unsubstituted or substituted heterocyclic rings consisting of a 4-6 membered unsaturated or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S; and n, p, q, r, and s are independently 0, 1, 2, 3, 4, 5 or 6;

provided that
when $R^9$ is $OCH_3$, $R^1$ is $CH_3$ and $R^5$ is $C(CH_3)_3$, then A is substituted,
when $R^9$ is hydrogen, $R^1$ is $CH_3$, and $R^5$ is hydrogen, then A is substituted,
when $R^9$ is hydrogen, $R^1$ is $CH_3$, and $R^5$ is $C(CH_3)_3$, then A is substituted, provided the substituent is not $CH_3$, and when $R^9$ is $OCH_3$, $R^1$ is $CH_3$, $R^5$ is $CH_3$, then A is substituted.

In a class of compounds of the invention, or pharmaceutically acceptable salts thereof, A is an aryl ring selected from phenyl, unsubstituted or substituted as defined above, or a heteroaryl ring, unsubstituted or substituted as defined above, selected from the group consisting of pyridine, pyrimidine, pyrazine, pyridazine, indole, pyrrolopyridine, benzimidazole, benzoxazole, benzothiazole, and benzoxadiazole;

$R^2$, $R^8$, $R^9$ and $R^{10}$ are independently selected from the group consisting of:
1) hydrogen,
2) halogen,
3) $OR^{43}$,
4) $(CR^eR^f)_pR^{43}$,
5) CN, and
6) $(CR^eR^f)_pC(O)N(R^{43}R^{44})$,
or $R^2$ and $R^8$ are independently as defined above, and $R^9$ and $R^{10}$, together with the atoms to which they are attached, form the ring

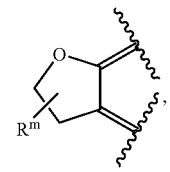

where $R^m$ is $C_{1-6}$alkyl;

$R^1$ is selected from the group consisting of
1) hydrogen,
2) $(CR^aR^b)_{1-2}R^{40}$
3) $(CR^aR^b)_{1-2}OR^{40}$,
4) $(CR^aR^b)_{1-2}N(R^{40}R^{41})$,
5) $(CR^aR^b)_{1-2}N(R^{40})C(O)OR^{41}$,
6) $(CR^aR^b)_{1-2}N(R^{40}) (CR^cR^d)_2N(R^{41})C(O)R^{49}$,
7) $(CR^aR^b)_{1-2}C(O)OR^{40}$,
8) $(CR^aR^b)_{1-2}N(R^{40}) (CR^cR^d)_{1-3}R^{41}$, and
9) cyclopropyl; and $R^5$ is selected from the group consisting of
1) hydrogen,
2) halogen,
3) $S(O)_{0-2}N(R^{53}R^{50})$,
4) $S(O)_{0-2}R^{62}$,
5) $CH_3$,
6) $C_3$-$C_6$ alkyl,
7) $C_3$-$C_{10}$ cycloalkyl,
8) $R^{82}$,
said alkyl, aryl, and cycloalkyl is unsubstituted, monosubstituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$, or $R^1$ and $R^5$ together with the atoms to which they are attached, form a ring selected from the group of structures consisting of

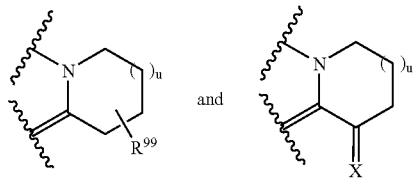 and 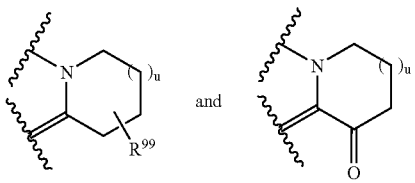

where u is 0 or 1, $R^{99}$ is hydrogen or —OH, and X is O or =NOH;

In a subclass of this class of compounds of the invention, or pharmaceutically acceptable salts thereof, $R^2$, $R^8$, $R^9$ and $R^{10}$ are independently selected from the group consisting of:
1) hydrogen,
2) halogen,
3) $OR^{43}$, and
4) $(CR^eR^f)_pC(O)N(R^{43}R^{44})$.

In a group of the subclass of compounds, or pharmaceutically acceptable salts thereof, $R^1$ is selected from the group consisting of
1) hydrogen,
2) $(CR^aR^b)_{1-2}R^{40}$
3) $(CR^aR^b)_{1-2}OR^{40}$, or
4) $(CR^aR^b)_{1-2}N(R^{40}R^{41})$;

$R^5$ is selected from the group consisting of
1) hydrogen,
2) $C_3$-$C_6$ alkyl, and
3) $CH_3$,
said alkyl is unsubstituted, mono-substituted with $R^{22}$, di-substituted with $R^{22}$ and $R^{23}$, tri-substituted with $R^{22}$, $R^{23}$ and $R^{24}$, or tetra-substituted with $R^{22}$, $R^{23}$, $R^{24}$ and $R^{25}$;

or $R^1$ and $R^5$ together with the atoms to which they are attached, form a ring selected from the group of structures consisting of

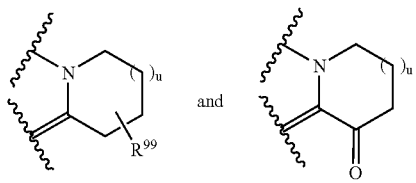

where u is 1, and $R^{99}$ is hydrogen or —OH.

In a subgroup of the group of compounds, or pharmaceutically acceptable salts thereof, A is unsubstituted phenyl, or phenyl substituted with halogen.

In a family of the subgroup of compounds, or pharmaceutically acceptable salts thereof, $R^1$ is selected from the group consisting of —$CH_3$, —$CH_2CH_3$, —$(CH_2)_2OCH_3$, —$(CH_2)_2NH_2$, and —$(CH_2)_3NH_2$, —$CH_2C(O)OC(CH_3)_3$; and $R^5$ is selected from the group consisting of hydrogen, —$C(CH_3)_3$, —$CH_3$, or $R^1$ and $R^5$ together with the atoms to which they are attached, form a ring selected from the group of structures consisting of where u is 1, and $R^{99}$ is hydrogen or —OH.

A preferred embodiment is a compound selected from the group consisting of
3-tert-butyl-4-(3-fluorophenyl)-6-methoxy-2-methylisoquinolin-1(2H)-one,
3-tert-butyl-4-(4-fluorophenyl)-6-methoxy-2-methylisoquinolin-1(2H)-one,
6-methoxy-2-methyl-4-phenylisoquinolin-1(2H)-one,
4-(3-fluorophenyl)-6-methoxy-2,3-dimethylisoquinolin-1(2H)-one,
4-(4-fluorophenyl)-6-methoxy-2,3-dimethylisoquinolin-1(2H)-one,
(1E)-11-(3-fluorophenyl)-9-methoxy-3,4-dihydro-2H-pyrido[1,2-b]isoquinoline-1,6-dione 1-oxime,
3-tert-butyl-6-hydroxy-2-methyl-4-phenylisoquinolin-1(2H)-one,
2,3-dimethyl-4-phenylisoquinolin-1(2H)-one,
3-tert-butyl-2-ethyl-6-methoxy-4-phenylisoquinolin-1(2H)-one,
3-tert-butyl-6-methoxy-4-phenylisoquinolin-1(2H)-one,
2-ethyl-6-methoxy-3-methyl-4-phenylisoquinolin-1(2H)-one,
6-methoxy-3-methyl-4-phenylisoquinolin-1(2H)-one,
6-methoxy-2-(2-methoxyethyl)-3-methyl-4-phenylisoquinolin-1 (2H)-one,
2-(2-aminoethyl)-6-methoxy-3-methyl-4-phenylisoquinolin-1(2H)-one,
2-(3-aminopropyl)-6-methoxy-3-methyl-4-phenylisoquinolin-1(2H)-one,
3-tert-butyl-2-methyl-1-oxo-4-phenyl-1,2-dihydroisoquinoline-6-carbonitrile,
3-tert-butyl-8-hydroxy-2-methyl-4-phenylisoquinolin-1(2H)-one,
3-tert-butyl-2-methyl-1-oxo-4-phenyl-1,2-dihydroisoquinoline-6-carboxamide,
3-tert-butyl-2-methyl-4-phenyl-6-(4-phenylbutoxy)isoquinolin-1(2H)-one,
3-tert-butyl-2-methyl-4-phenyl-6-[(5-phenylpentyl)oxy]isoquinolin-1(2H)-one,
11-(3-fluorophenyl)-9-methoxy-3,4-dihydro-2H-pyrido[1,2-b]isoquinoline-1,6-dione,
(+/−)-11-(3-fluorophenyl)-1-hydroxy-9-methoxy-1,2,3,4-tetrahydro-6H-pyrido[1,2-b]isoquinolin-6-one,
(1S)-11-(3-fluorophenyl)-1-hydroxy-9-methoxy-1,2,3,4-tetrahydro-6H-pyrido[1,2-b]isoquinolin-6-one,
(1R)-11-(3-fluorophenyl)-1-hydroxy-9-methoxy-1,2,3,4-tetrahydro-6H-pyrido[1,2-b]isoquinolin-6-one, and
11-(3-fluorophenyl)-9-methoxy-1,2,3,4-tetrahydro-6H-pyrido[1,2-b]isoquinolin-6-one, or a pharmaceutically acceptable salt thereof.

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppresant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an anti-tachycardia device (e.g. a defibrillator or a pacemaker) in combination with a compound of Claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have asymmetric centers or asymmetric axes, and this invention includes all of the optical isomers and mixtures thereof. Unless specifically mentioned otherwise, reference to one isomer applies to both isomers.

In addition compounds with carbon-carbon double bonds may occur in Z- and E-forms with all isomeric forms of the compounds being included in the present invention.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetylene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

Unless otherwise noted, alkyl, alkenyl and alkynyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

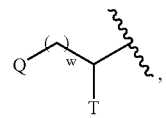

wherein w is an integer equal to zero, 1 or 2, the structure is

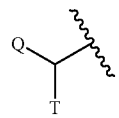

when w is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

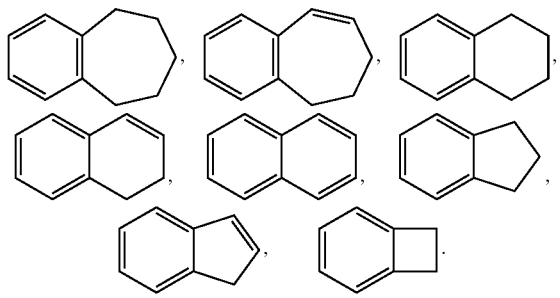

The term "aryl" refers to aromatic mono- and poly-carbocyclic ring systems, wherein the individual carbocyclic rings in the poly ring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

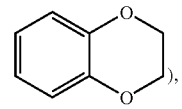

), imidazo(2,1-b)(1,3)thiazole, (i.e.,

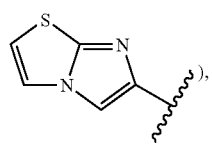

and benzo-1,3-dioxolyl (i.e.,

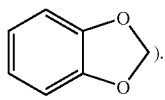

In certain contexts herein,

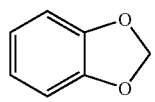

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

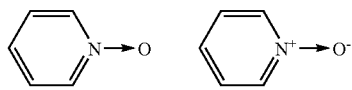

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

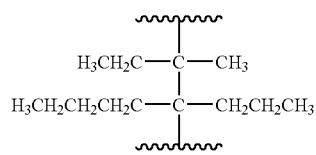

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes, in which variables $R^1$, $R^5$ and $R^9$ are as defined above, and variable $R^3$ is a substituent selected from the group of substituents listed above as possible substituents when A is a substituted aryl ring. Other synthetic protocols will be readily apparent to those skilled in the art.

Scheme 1

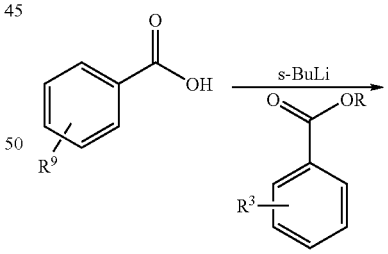

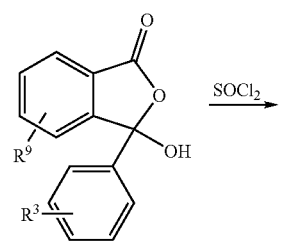

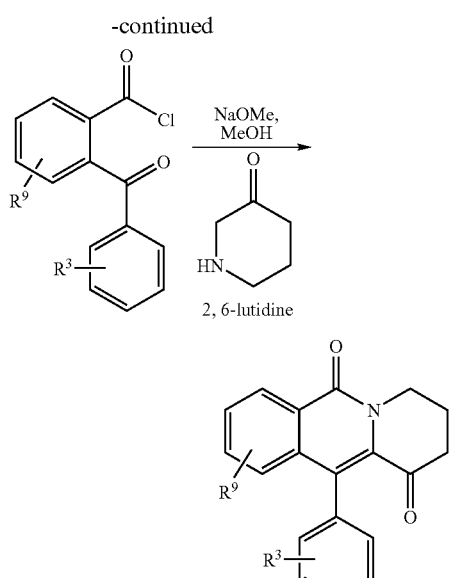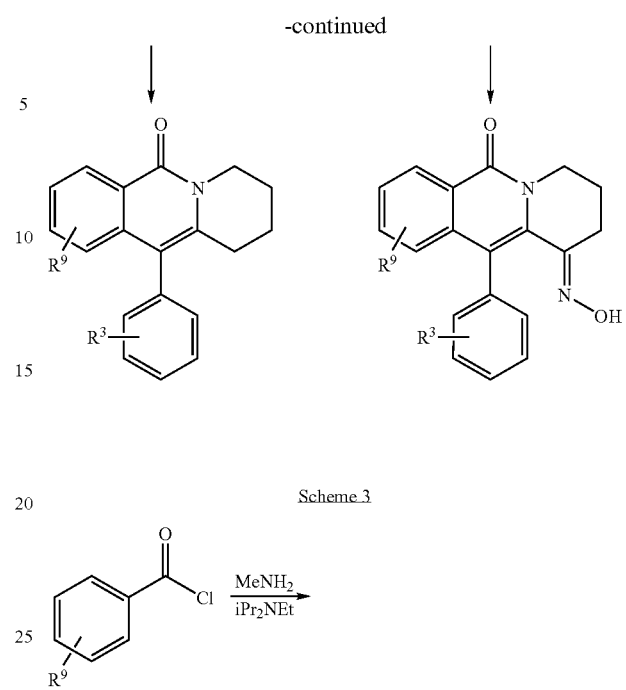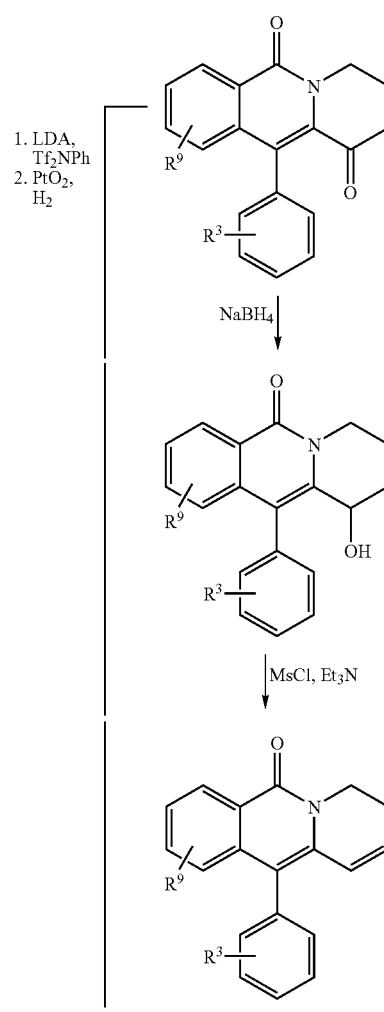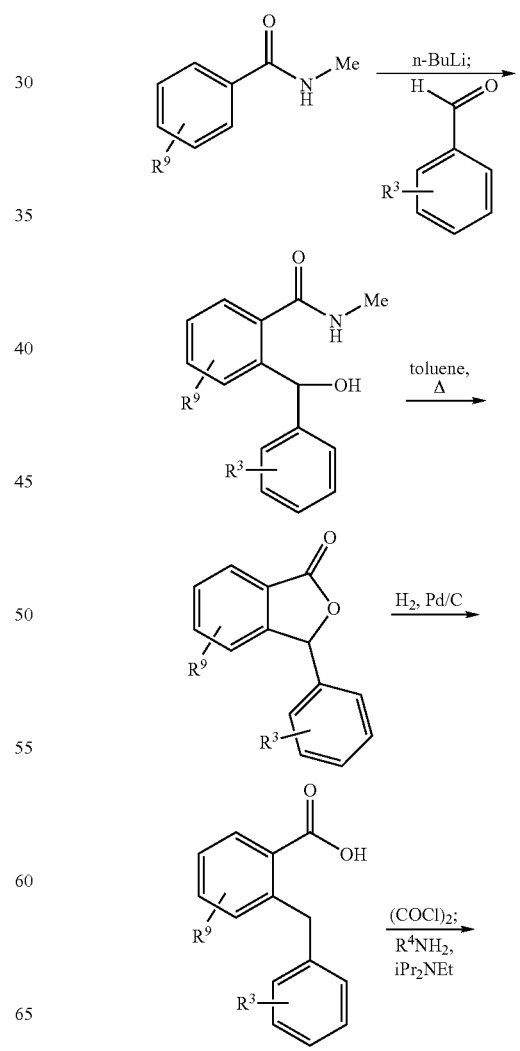

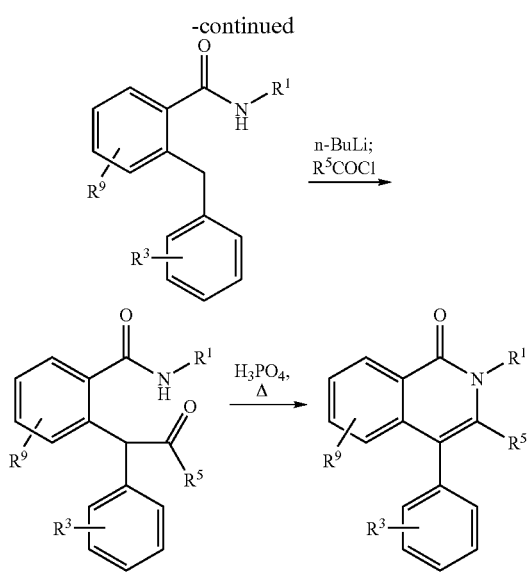

The following examples illustrate the preparation of the compounds of Formula I and as such are not to be considered as limiting the invention set forth in the claims appended hereto.

Example 1

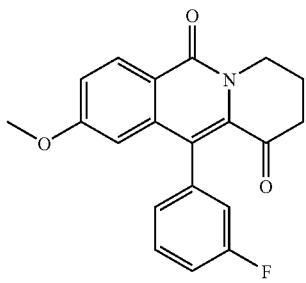

11-(3-fluorophenyl)-9-methoxy-3,4-dihydro-2H-pyrido[1,2-b]isoquinoline-1,6-dione To a mixture of 2-(3-fluorobenzoyl)-4-methoxybenzoyl chloride (3.36 g) and piperidin-3-one hydrochloride (1.88 g) in 54 ml of toluene was added 2,6-lutidine (4.01 ml). The reaction was heated at reflux (3:10 pm) for 24 h, then partitioned between EtOAc and 400 mL of 1 N HCl. The aqueous solution was extracted twice more with EtOAc. The combined organic solutions were dried (MgSO$_4$) and concentrated. Flash chromatography (40-100% EtOAc/hexanes) to gave the titled compound.

HRMS (ES): calcd: 338.1187. found: 338.1188.

Example 2

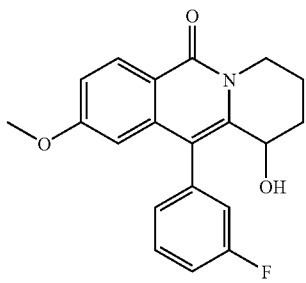

11-(3-fluorophenyl)-1-hydroxy-9-methoxy-1,2,3,4-tetrahydro-6H-pyrido[1,2-b]isoquinolin-6-one To a solution of 11-(3-fluorophenyl)-9-methoxy-3,4-dihydro-2H-pyrido[1,2-b]isoquinoline-1,6-dione in 5 mL 1:1 MeOH:CH$_2$Cl$_2$ was added NaBH$_4$ (17 mg). The reaction was stirred at room temp for 1 h, then diluted with bicarb and EtOAc and stirred for 30 min. The mixture was extracted once with EtOAc, and the organic solution was washed once with brine, dried (Na$_2$SO$_4$) and concentrated. Flash chromatography (40 g silica, 50-100% EtOAc/hexanes) gave the titled compound.

HRMS (ES): calcd: 340.1343. found: 340.1353.

11-(3-fluorophenyl)-1-hydroxy-9-methoxy-1,2,3,4-tetrahydro-6H-pyrido[1,2-b]isoquinolin-6-one was resolved into its constituent enantiomers by chiral HPLC. The two pure enantiomers were identical to the racemic compound by HRMS and NMR.

Example 3

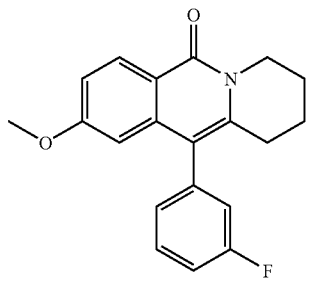

11-(3-fluorophenyl)-9-methoxy-1,2,3,4-tetrahydro-6H-pyrido[1,2-b]isoquinolin-6-one Step A A suspension of 11-(3-fluorophenyl)-9-methoxy-3,4-dihydro-2H-pyrido[1,2-b]isoquinoline-1,6-dione in 2 ml of THF and 2 mL of TMEDA was cooled to 0 C and treated lithium diisopropylamide solution (Aldrich, 2 M, 0.445 mL). After stirring for 1 h, a solution of Tf$_2$NPh in 2 ml THF/2 ml TMEDA was added via cannula. The reaction was warmed to room temp and stirred for 2 h, then partitioned between CH$_2$Cl$_2$ and pH 7 buffer. The aqueous solution was extracted once more with CH$_2$Cl$_2$. The combined organic solutions were dried (Na$_2$SO$_4$) and concentrated, then purified by flash chromatography (40 g silica, 30-90% EtOAc/hexanes) to give 57 mg of 11-(3-fluorophenyl)-9-methoxy-6-oxo-3,6-dihydro-4H-pyrido[1,2-b]isoquinolin-1-yl trifluoromethanesulfonate.

Step B

To a suspension of 11-(3-fluorophenyl)-9-methoxy-6-oxo-3,6-dihydro-4H-pyrido[1,2-b]isoquinolin-1-yl trifluoromethanesulfonate in EtOH (4 ml) and EtOAc (2 mL) was added PtO$_2$ as a slurry in EtOH. The reaction was stirred at room temp under an H$_2$ balloon for 16 h. The mixture was filtered through celite and concentrated. Flash chromatography (40 g silica, 30-80% EtOAc/hexanes) gave the titled compound.

HRMS (ES): calcd: 324.1395. found: 324.1394.

Example 4

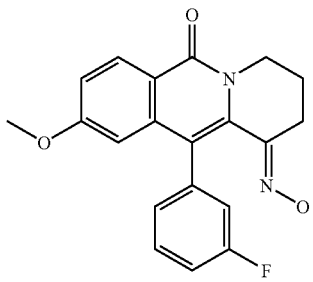

(1E)-11-(3-fluorophenyl)-9-methoxy-3,4-dihydro-2H-pyrido[1,2-b]isoquinoline-1,6-dione 1-oxime To a solution of 11-(3-fluorophenyl)-9-methoxy-3,4-dihydro-2H-pyrido[1,2-b]isoquinoline-1,6-dione (125 mg) in 4 mL pyridine was added hydroxylamine hydrochloride (51 mg). The reaction was heated to reflux for 5 h, then cooled to room temp and partitioned between ether and water. The aqueous solution was extracted with ether (2×). The combined organic solutions were washed with 1 N HCl (1×), and 10% bicarb (1×), then dried (MgSO$_4$) and concentrated. Flash chromatography (10-70% EtOAc/hexanes) gave the titled compound.

HRMS (ES): calcd: 353.1296. found: 353.1305.

Example 5

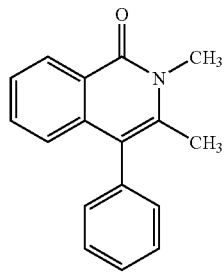

2,3-Dimethyl-4-phenyl-2H-isoquinolin-1-one

Step A

To a stirred solution of α-phenyl-o-toluic acid (2.0 g, 9.43 mmol) in methylene chloride (500 mL) at room temperature under argon was added by dropwise addition a solution of oxalyl chloride (0.988 mL, 11.3 mmol) in methylene chloride (50 mL). N,N-Dimethylformamide (10 drops) were added and the contents of the reaction flask were stirred 1.5 h. Solvent was removed in vacuo and methylene chloride (100 mL) and methylamine hydrochloride (950 mg, 14.1 mmol) was added. With ice-bath cooling a solution of N,N-diisopropylethylamine (4.10 mL, 23.6 mmol) in methylene chloride (10 mL) was added dropwise. Saturated sodium bicarbonate was added and the resulting mixture extracted with methylene chloride (3×). The combined organic extracts were dried with sodium sulfate (anh.). Filtration followed by removal of the solvent in vacuo gave a solid which after trituration with ether afforded N-Methyl-2-(phenylmethyl) benzamide (974 mg, 4.23 mol, 46%). MS [M+H]$^+$226

Step B

To an isopropanol/dry ice cooled solution of N-Methyl-2-(phenylmethyl) benzamide (1.00 g, 4.44 mmol) in THF (20 mL) under argon was added n-butyllithium solution (2.5M, 4.44 mL, 11.1 mmol) dropwise. After 10 min. neat acetyl chloride (0.447 mL, 6.66 mmol) was slowly added to the reaction solution. The contents of the reaction flask were allowed to warm to room temperature and after 2 h the reaction was quenched with saturated ammonium chloride. The mixture was extracted with ether (3×) and then the combined organic portions were washed with brine and dried with anhydrous sodium sulfate. Filtration followed by evaporation of solvent in vacuo gave the crude product which was subjected to flash column chromatography (hexane:ethyl acetate 70:30 then 50:50) to afford the title compound as a white solid.

MS [M+H]$^+$250

$^1$HNMR (CHCl$_3$, 300 MHz) δ 8.48 (m, 1H); 7.54-7.38 (m, 5H); 7.28-7.20 (m, 2H); 6.98 (m, 1H), 3.70 (s, 3H); 2.21 (s, 3H).

Example 6

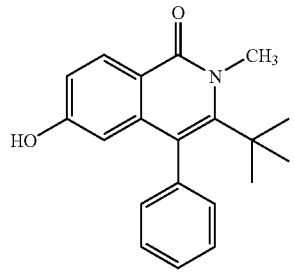

3-tert-Butyl-6-hydroxy-2-methyl-4-phenyl-2H-isoquinolin-1-one

To a methylene chloride (5 mL) solution of 3-tert-butyl-6-methoxy-2-methyl-4-phenylisoquinolin-1(2H)-one (100 mg, 0.311 mmol) under argon at −70° C. was added boron tribromide (1.0M, 0.934 mL, 0.934 mmol). The contents of the reaction flask were warmed to room temperature and stirred 24 h. Extracted with methylene chloride (3×), then the combined organic extracts were washed with brine and dried with anhydrous sodium sulfate. Filtration followed by evaporation of solvent in vacuo gave a solid which was triturated with ethanol. Recrystallization from ethyl acetate/ethanol afforded the title compound.

MS [M+H]$^+$308

$^1$HN MR (CDCl$_3$, 300 MHz) δ 9.21 (s, 1H); 8.27 (d, 1H); 7.45-7.25 (m, 3H); 7.28-7.22 (m, 2H), 6.95 (dd, 1H); 6.23 (m, 1H); 3.74 (s, 3H); 1.35 (s, 9H).

Example 7

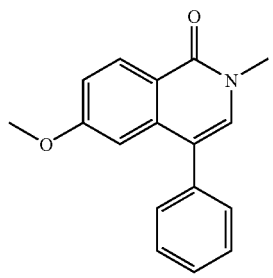

6-methoxy-2-methyl-4-phenylisoquinolin-1(2H)-one

Step A

A solution of 2-benzyl-4-methoxy-N-methylbenzamide (125 mg) in 5 mL THF was cooled to −78 C. n-BuLi (0.400 mL, 2.5 M in hexanes) was added, and the reaction was stirred at −78 C for 20 min. A solution of ethyl formate (0.160 mL) in 1 mL THF was added via cannula. The reaction was quenched at −78 C by addition of saturated aqueous ammonium acetate. The mixture was extracted with EtOAc and concentrated to give 4-methoxy-N-methyl-2-(2-oxo-1-phenylethyl)benzamide, which was used without further purification.

Step B 4-methoxy-N-methyl-2-(2-oxo-1-phenylethyl)benzamide (100 mg) was dissolved in 2 mL of phosphoric acid with gentle heating. After a solution was obtained, the reaction was partitioned between water and EtOAc. The organic solution was dried ($Na_2SO_4$) and concentrated. Flash chromatography (25% EtOAc in $CH_2Cl_2$) provided the titled compound as a white solid.

$[M+H]^+$ calcd: 266. found: 266 (FAB).

Example 8

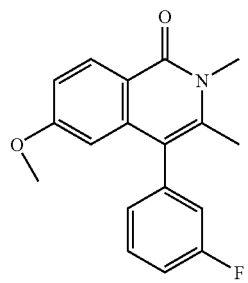

4(3-fluorophenyl)-6-methoxy-2,3-dimethylisoquinolin-1(2H)-one

Step A

To a −78 C solution of 4-methoxy-N-methylbenzamide (2.0 g) in THF was added n-BuLi (10 mL, 2.5 M in hexanes). The reaction was stirred for 10 min at −78° C., warmed to 0 C, then cooled back to −78 C. 3-fluorobenzaldehyde (1.90 mL) was added as a solution in THF via cannula. The reaction was warmed to room temp, then quenched with saturated aqueous $NH_4Cl$. The mixture was extracted with EtOAc, concentrated, and purified by flash chromatography (5% MeOH in $CH_2Cl_2$) to give 2-[(3-fluorophenyl) (hydroxy)methyl]-4-methoxy-N-methylbenzamide.

Step B

To a solution of 2-[(3-fluorophenyl)(hydroxy)methyl]-4-methoxy-N-methylbenzamide (500 mg) in methanol was added 500 mg of Pd/C (10%). The reaction was stirred overnight under $H_2$ (1 atm), then filtered through celite and concentrated to give 2-(3-fluorobenzyl)-4-methoxy-N-methylbenzamide, which was used without further purification.

Step C

To a −78 C solution of 2-(3-fluorobenzyl)-4-methoxy-N-methylbenzamide (500 mg) in 15 mL THF was added n-BuLi (1.64 mL, 2.5 M in hexanes) dropwise. After 10 min, acetyl chloride (170 mg) was added as a solution in 2 mL THF. The cooling bath was removed, and the reaction was stirred for 2 h. The reaction was quenched with saturated aqueous $NH_4Cl$ and extracted with EtOAc. The organic solution was concentrated and treated with phosphoric acid and minimal $CH_2Cl_2$ until a solution was obtained. Removal of $CH_2Cl_2$ was followed by addition of bicarb/EtOAc to neutralize the reaction. The mixture was extracted with EtOAc, concentrated, and purified by flash chromatography (20% EtOAc in $CH_2Cl_2$) to give a solid, which was triturated with EtOAc to give the titled compound.

$[M]^+$ calcd: 297. found: 297 (EI).

Example 9

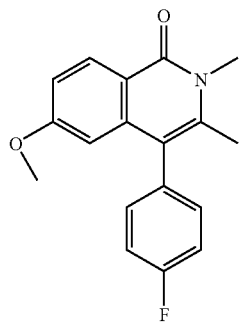

4-(4-fluorophenyl)-6-methoxy-2,3-dimethylisoquinolin-1(2H)-one

Following the procedure for 4-(3-fluorophenyl)-6-methoxy-2,3-dimethylisoquinolin-1(2H)-one, using (in Step A) 4-fluorobenzaldehyde in place of 3-fluorobenzaldehyde, the title compound was synthesized.

$[M]^+$ calcd: 297. found: 297 (EI).

Example 10

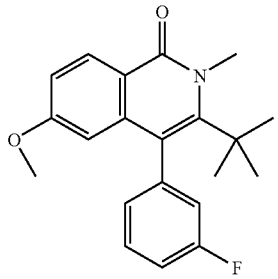

3-tert-butyl-4-(3-fluorophenyl)-6-methoxy-2-methylisoquinolin-1(2H)-one

Following the procedure for 4-(3-fluorophenyl)-6-methoxy-2,3-dimethylisoquinolin-1(2H)-one, using (in Step C) pivaloyl chloride in place of acetyl chloride, and heating (in Step C) the final phosphoric acid solution to 100 C, the title compound was synthesized.

$[M]^+$ calcd: 339. found: 339 (EI).

Example 11

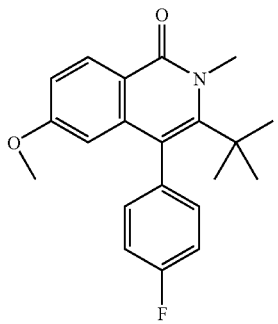

3-tert-butyl-4-(4-fluorophenyl)-6-methoxy-2-methyl-isoquinolin-1(2H)-one

Following the procedure for 4-(3-fluorophenyl)-6-methoxy-2,3-dimethylisoquinolin-1(2H)-one, using (in Step A) 4-fluorobenzaldehyde in place of 3-fluorobenzaldehyde, using (in Step C) pivaloyl chloride in place of acetyl chloride, and heating (in Step C) the final phosphoric acid solution to 100 C, the title compound was synthesized.

$[M]^+$ calcd: 339. found: 339 (EI).

Example 12

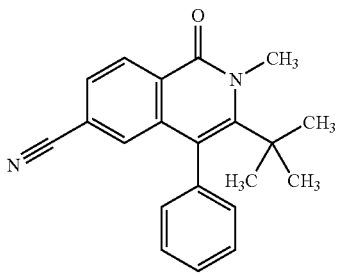

3-tert-butyl-2-methyl-1-oxo-4-phenyl-1,2-dihydroisoquinoline-6-carbonitrile

Step A
A mixture of 3-tert-butyl-6-methoxy-2-methyl-4-phenyl-isoquinolin-1(2H)-one (0.333 g) and 48% HBr (30 mL) was heated at reflux for 8 h. The reaction was concentrated to give 3-tert-butyl-6-hydroxy-2-methyl-4-phenylisoquinolin-1(2H)-one as a brown solid, which was used without further purification.

Step B
To a solution of 3-tert-butyl-6-hydroxy-2-methyl-4-phenylisoquinolin-1(2H)-one (210 mg) in 7 mL DMP were added potassium carbonate (281 mg) and N-phenyl triflimide (731 mg). The reaction was stirred at room temp for 90 min, then partitioned between water and EtOAc. The organic solution was dried ($Na_2SO_4$) and concentrated, then purified by flash chromatography (20% EtOAc in hexanes) to give 175 mg of 3-tert-butyl-2-methyl-1-oxo-4-phenyl-1,2-dihydroisoquinolin-6-yl trifluoromethanesulfonate.

Step C
A solution of 3-tert-butyl-2-methyl-1-oxo-4-phenyl-1,2-dihydroisoquinolin-6-yl trifluoromethanesulfonate (225 mg) in 3 mL DMF was sparged with Argon for 10 min. $Zn(CN)_2$ (250 mg) and $Pd(PPh_3)_4$ (100 mg) were added, and the reaction was heated at 80 C for 5 h, then partitioned between toluene and 2 N NaOH. The organic solution was washed with 2 N NaOH (2×), then dried ($Na_2SO_4$) and concentrated. Flash chromatography (20% EtOAc in hexanes) gave the titled compound.

Elemental analysis calcd for $C_{21}H_{20}N_2O$-0.45$H_2O$-0.05 EtOAc: C, 77.41; H, 6.53; N, 8.52. found: C, 77.36; H, 6.45; N, 8.53.

Example 13

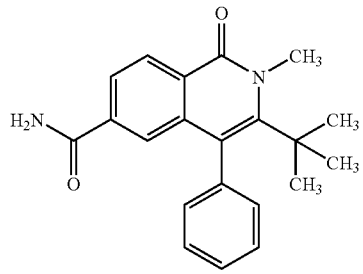

3-tert-butyl-2-methyl-1-oxo-4-phenyl-1,2-dihydroisoquinoline-6-carboxamide 3-tert-butyl-2-methyl-1-oxo-4-phenyl-1,2-dihydroisoquinoline-6-carbonitrile (300 mg), 10 N NaOH (6 mL), and methanol (1 mL) were combined at heated at 110 C overnight. The reaction was acidified with 6 N HCl to give a precipitate, which was isolated by filtration. This material was partitioned between EtOAc and 1 N NaOH by stirring vigorously overnight. The organic solution was discarded, and the aqueous solution was allowed to stand overnight, during which time a precipitate formed. Filtration provided the titled compound.

$[M+H]^+$ calcd: 335. found: 335 NAB).

Example 14

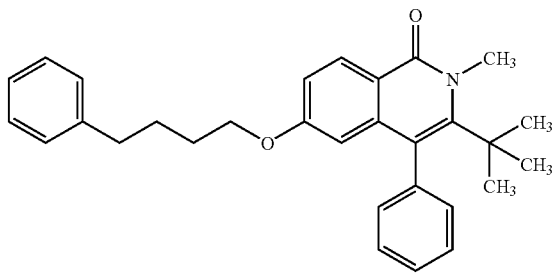

3-tert-butyl-2-methyl-4-phenyl-6-(4-phenylbutoxy)isoquinolin-1(2H)-one

A solution of 3-tert-butyl-6-hydroxy-2-methyl-4-phenyl-isoquinolin-1(2H)-one (50 mg), 4-phenyl-1-iodobutane (100 mg) and cesium carbonate (100 mg) in DMF (2.5 mL) was heated at 80 C for 6 h. The reaction was partitioned between water and EtOAc. The organic solution was dried ($Na_2SO_4$) and concentrated, then purified by flash chromatography (20% EtOAc in hexanes) to give the titled compound.

$[M+H]^+$ calcd: 440. found: 440 (FAB).

Example 15

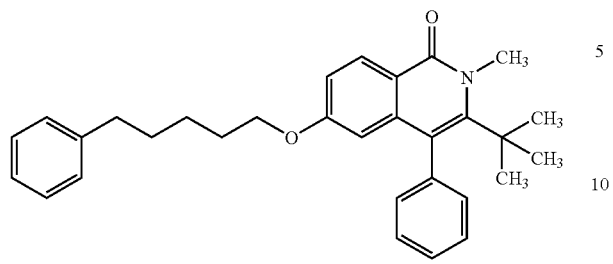

3-tert-butyl-2-methyl-4-phenyl-6-[(5-phenylpentyl)oxy]isoquinolin-1(2H)-one

Following the procedure for 3-tert-butyl-2-methyl-4-phenyl-6-(4-phenylbutoxy)isoquinolin-1(2H)-one, using 5-phenyl-1-iodopentane in place of 4-phenyl-1-iodobutane, the titled compound was obtained.

$^1$H NMR (CDCl$_3$, 300 MHz) δ 8.34 (d, J=9 Hz, 1H); 7.40 (m, 2H); 7.29-7.14 (m, 8H); 6.95 (dd, J=9.2 Hz, 1H); 6.14 (d, J=2 Hz, 1H); 3.75 (s, 3H); 3.71-3.75 (m, 2H); 2.59 (t, J=8 Hz, 2H); 1.72-1.56 (m, 4H); 1.44-1.33 (m, 2H); 1.27 (s, 9H)

Example 16

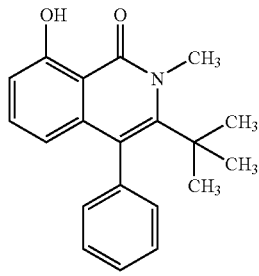

3-tert-butyl-8-hydroxy-2-methyl-4-phenylisoquinolin-1(2H)-one

Step A

Following the procedure for 4-(3-fluorophenyl)-6-methoxy-2,3-dimethylisoquinolin-1(2H)-one, using (in Step A) 2-methoxy-N-methylbenzamide in place of 4-methoxy-N-methylbenzamide, using (in Step C) pivaloyl chloride in place of acetyl chloride, and heating (in Step C) the final phosphoric acid solution to 100 C, 3-tert-butyl-8-methoxy-2-methyl-4-phenylisoquinolin-1(2H)-one was synthesized.

Step B

A mixture of 3-tert-butyl-8-methoxy-2-methyl-4-phenylisoquinolin-1(2H)-one (0.500 g) and 48% HBr (15 mL) was heated at reflux overnight. The reaction was concentrated and purified by flash chromatography (10% EtOAc in hexanes) to give the titled compound.

Elemental analysis calcd for C$_{20}$H$_{21}$NO$_2$-0.10H$_2$O-0.10 EtOAc: C, 77.04; H, 6.97; N, 4.40. found: C, 77.04; H, 6.97; N, 4.40.

Example 17

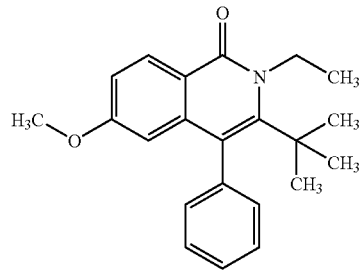

3-tert-butyl-2-ethyl-6-methoxy-4-phenylisoquinolin-1(2H)-one

Step A

To a 0 C solution of 2-benzyl-4-methoxybenzoic acid (5 g) in 250 mL CH$_2$Cl$_2$ were added a catalytic amount of DMF and a solution of oxalyl chloride (2 mL) in 40 mL CH$_2$Cl$_2$. The reaction was warmed to room temp and stirred overnight, then concentrated to dryness and azeotroped from toluene (2×). The residue was dissolved in 50 mL THF and added dropwise to a 0 C solution of ethylamine (10 mL, 70% aqueous solution) in 200 mL THF. The reaction was warmed to room temp and stirred for 2 h, then quenched with saturated aqueous KHSO$_4$ solution and extracted with EtOAc (2×). The organic solutions were dried (Na$_2$SO$_4$) and concentrated, then triturated with hexanes to give 5.2 g of 2-benzyl-N-ethyl-4-methoxybenzamide.

Step B

Following the procedure for 4-(3-fluorophenyl)-6-methoxy-2,3-dimethylisoquinolin-1(2H)-one (Step C), using 2-benzyl-N-ethyl-4-methoxybenzamide in place of 2-(3-fluorobenzyl)-4-methoxy-N-methylbenzamide, using pivaloyl chloride in place of acetyl chloride, and heating the final phosphoric acid solution to 100 C, the titled compound was synthesized.

Elemental analysis calcd for C$_{22}$H$_{25}$NO$_2$-0.35H$_2$O: C, 77.31; H, 7.58; N, 4.10. found: C, 77.32; H, 7.29; N, 3.83.

Example 18

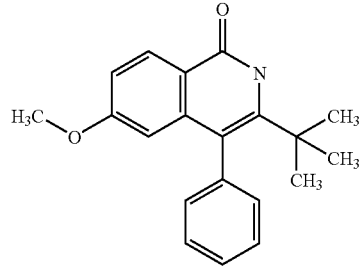

3-tert-butyl-6-methoxy-4-phenylisoquinolin-1(2H)-one

Step A

To a solution of 2-benzyl-4-methoxybenzoic acid (14.2 g) in 600 mL CH$_2$Cl$_2$ was added a catalytic amount of DMF, followed by a solution of oxalyl chloride (8.7 g) in 100 mL of CH₂Cl₂. The reaction was stirred at room temp overnight, then concentrated and azeotroped with toluene (2×). The residue was dissolved in 700 mL CH₂Cl₂ and cooled to 0 C. Tert-butyl amine (13.9 g) was added, and the reaction was warmed to room temp. After 1.5 h, the reaction was quenched with 5% aqueous KHSO₄. The organic solution was separated, washed once with saturated aqueous sodium bicarbonate, dried (Na₂SO₄) and concentrated to give 15.9 g of 2-benzyl-N-tert-butyl)-4-methoxybenzamide.

Step B

A solution of 2-benzyl-N-(tert-butyl)-4-methoxybenzamide (3.1 g) in 50 mL THF was sparged with Ar for 10 min. The solution was cooled to −78 C, and n-BuLi (10 mL of a 2.5 M hexanes solution) was added dropwise. After stirring for 1 h at −78 C, pivaloyl chloride (0.99 g) was added dropwise. The reaction was stirred for 10 min at −78 C, then for 1 h at room temp, then quenched with saturated aqueous NH₄Cl. The mixture was extracted with EtOAc (3×), then the combined organic solutions were washed with brine (1×), dried (Na₂SO₄) and concentrated. The residue was combined with 25 mL of 80% H₃PO₄ and heated to 100 C for 3 h. The reaction was poured into ice, then extracted with $CH_2Cl_2$ (3×). The organic solutions were washed with saturated aqueous sodium bicarbonate, dried (Na₂SO₄) and concentrated. Trituration with diethyl ether provided 2.7 g of the titled compound.

Elemental analysis calcd for C₂₀H₂₁NO₂: C, 78.14; H, 6.89; N, 4.56. found: C, 77.81; H, 6.77; N, 4.65.

Example 19

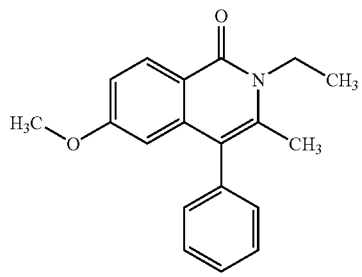

2-ethyl-6-methoxy-3-methyl-4-phenylisoquinolin-1 (2H)-one

Following the procedure for 4-(3-fluorophenyl)-6-methoxy-2,3-dimethylisoquinolin-1(2H)-one (Step C), using 2-benzyl-N-ethyl-4-methoxybenzamide in place of 2-(3-fluorobenzyl)-4-methoxy-N-methylbenzamide and heating the final phosphoric acid solution to 100 C, the titled compound was synthesized.

[M+H]⁺ calcd: 294. found: 294 (FAB)

Example 20

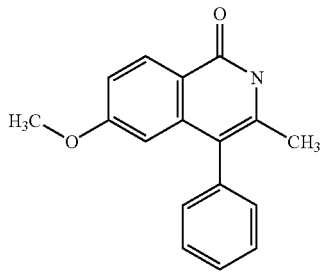

6-methoxy-3-methyl-4-phenylisoquinolin-1(2H)-one

A solution of 2-benzyl-N-(tert-butyl)-4-methoxybenzamide (3.1 g) in 50 mL THF was sparged with Ar for 10 min. The solution was cooled to −78 C, and n-BuLi (10 mL of a 2.5 M hexanes solution) was added dropwise. After stirring for 1 h at −78 C, acetyl chloride (0.99 g) was added dropwise. The reaction was stirred for 10 min at −78 C, then for 1 h at room temp, then quenched with saturated aqueous NH₄Cl. The mixture was extracted with EtOAc (3×), then the combined organic solutions were washed with brine (1×), dried (Na₂SO₄) and concentrated. The residue was combined with 25 mL of 80% H₃PO₄ and heated to 100 C for 3 h. The reaction was poured into ice, then extracted with CH₂Cl₂ (3×). The organic solutions were washed with saturated aqueous sodium bicarbonate, dried (Na₂SO₄) and concentrated. Trituration with diethyl ether provided the titled compound.

Elemental analysis calcd for C₁₇H₁₅NO₂·1.0H₂O: C, 72.06; H, 6.05; N, 4.94. found: C, 72.40; H, 5.52; N, 4.61.

Example 21

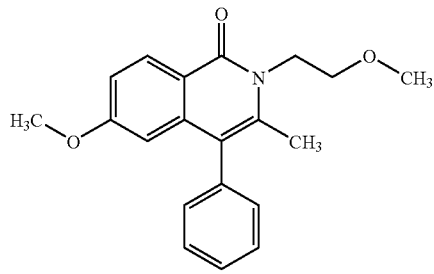

6-methoxy-2-(2-methoxyethyl)-3-methyl-4-phenyl-isoquinolin-1(2H)-one

A combination of 6-methoxy-3-methyl-4-phenylisoquinolin-1(2H)-one (0.85 g) and sodium hydride (60% dispersion in mineral oil, 240 mg) in 25 mL of DMF was heated at 60 C for 30 min, then cooled to room temp. 4-bromo-1-methoxyethane (1 mL) was added via syringe, and the reaction was stirred at room temp overnight, then quenched by addition of saturated aqueous NH₄Cl. The mixture was extracted with EtOAc (3×). The combined organic solutions were washed with water (1×) and brine (1×), then dried (Na₂SO₄) and concentrated. Flash chromatography (20% EtOAc/hexanes) gave a solid which was triturated with diethyl ether to provide the titled compound.

Elemental analysis calcd for C₂₀H₂₁NO₃: C, 74.28; H, 6.55; N, 4.33. found: C, 74.43; H, 6.58; N, 4.18.

Example 22

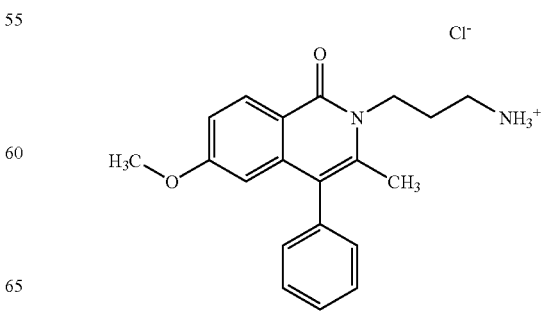

3-(6-methoxy-3-methyl-1-oxo-4-phenylisoquinolin-2(1H)-yl)propan-1-aminium chloride Step A A combination of 6-methoxy-3-methyl-4-phenylisoquinolin-1(2H)-one (0.85 g) and sodium hydride (60% dispersion in mineral oil, 186 mg) in 25 mL of DMF was heated at 60 C for 30 min, then cooled to room temp. 3-phthalimido-1-bromopropane (1 mL) was added via syringe, and the reaction was stirred at room temp overnight, then quenched by addition of saturated aqueous $NH_4Cl$. The mixture was extracted with EtOAc (3×). The combined organic solutions were washed with water (1×) and brine (1×), then dried ($Na_2SO_4$) and concentrated. Flash chromatography (20% EtOAc/hexanes) gave a solid which was triturated with diethyl ether to provide 500 mg of 2-[3-(6-methoxy-3-methyl-1-oxo-4-phenylisoquinolin-2(1H)-yl)propyl]-1H-isoindole-1,3(2H)-dione.

Step B

2-[3-(6-methoxy-3-methyl-1-oxo-4-phenylisoquinolin-2(1H)-yl)propyl]-1H-isoindole-1,3(2H)-dione (0.46 g) was dissolved in 20 mL methanol, and hydrazine (0.100 mL) was added. The reaction was stirred overnight at room temp, then diluted with brine and extracted with EtOAc (3×). The combined organic solutions were dried ($Na_2SO_4$) and concentrated. Flash chromatography (5% MeOH in $CH_2Cl_2$) gave a solid, which was treated with excess HCl and recrystallized from isopropanol/diethyl ether to give the titled compound.

Elemental analysis calcd for $C_{20}H_{22}N_2O_2$—HCl: C, 66.93; H, 6.46; N, 7.81. found: C, 66.57; H, 6.41; N, 7.47.

Example 23

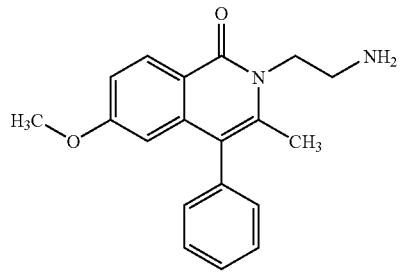

2-(2-aminoethyl)-6-methoxy-3-methyl-4-phenylisoquinolin-1(2H)-one

Step A

Following the procedure for 2-[3-(6-methoxy-3-methyl-1-oxo-4-phenylisoquinolin-2(1H)-yl)propyl]-1H-isoindole-1,3(2H)-dione, using 2-(Boc-amino) ethyl bromide in place of 3-phthalimido-1-bromopropane, tert-butyl 2-(6-methoxy-3-methyl-1-oxo-4-phenylisoquinolin-2(1H)-yl)ethylcarbamate was obtained.

Step B tert-butyl 2-(6-methoxy-3-methyl-1-oxo-4-phenylisoquinolin-2(1H)-yl)ethylcarbamate (800 mg) was dissolved in 200 mL EtOAc and cooled to 0 C. HCl gas was bubbled through the solution for 5 min, and the reaction was warmed to room temp. After stirring for 4 h, the reaction was filtered to isolate the hydrochloride salt of the title compound as a white solid.

$[M+H]^+$ calcd: 309. found: 309 (FAB).

The following additional compounds were prepared using procedures generally described above, e.g. Examples 1 and 2.

| Example | Compound | Name | MS (M+1) |
|---|---|---|---|
| 24 | | 10-(3-chlorophenyl)-8-methoxy-2,3-dihydropyrrolo[1,2-b]isoquinoline-1,5-dione | 340.0732 |
| 25 | | 10-(3-chlorophenyl)-1-hydroxy-8-methoxy-2,3-dihydropyrrolo[1,2-b]isoquinolin-5(1H)-one Enantiomer A | 342.0879 |

-continued

| Example | Compound | Name | MS (M+1) |
|---|---|---|---|
| 26 | (structure) | 10-(3-chlorophenyl)-1-hydroxy-8-methoxy-2,3-dihydropyrrolo[1,2-b]issoquinolin-5(1H)-one Enantiomer B | 342.0879 |

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward K$^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K$^+$ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the 10$^{th}$ pulse than for the 1$^{st}$ pulse of the train. A Kv1.5 blocker may exhibit both use-dependence and rate-dependence.

A Kv1.5 blocker may also be identified through electrophysiological studies of native I$_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2): 127-135, 2003) and Schroeder et al. (J. of Biomol. Screen., 8(1);50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 μg/ml streptomycin, 1000 μg/ml G-418 sulfate. Cells are subcultured by treatment with Versene, then suspended in phosphate-buffered saline (PBS) and centrifuged The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxylethylpiperazine-N$^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, KPO$_4$ 1.47, MgCl$_2$ 0.50, NaCl 138, NaPO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS ~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 μL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the 27$^{th}$ depolarization to +40 mV (in the 5 Hz train) is plotted as a function of antagonist concentration. The concentrations of drug required to inhibit current by 50% (IC$_{50}$) are determined by fitting of the Hill equation to the concentration response data: % of Control=100×(1+([Drug]/IC$_{50}$)$^p$)$^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the 1$^{st}$ depolarization to +40 mV minus the pre-compound mean current amplitude during the 27$^{th}$ depolarization to +40 mV)
4) peak current (maximum current amplitude during the 27$^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide ≧20% inhibition at a concentration of 33 μM or less in the high throughput Kv1.5 planar patch clamp assay described above.

Atomic Absorption Spectroscopy Protocol:

This assay identifies agents that specifically block the human Kv1.5 K+ channel heterologously expressed in CHO cells as measured by Rb$^+$ efflux using Flame Atomic Absorption Spectroscopy (FAAS). The application of FAAS for measuring ion channel activity was adapted from Terstappen et al, *Anal. Biochem*, 272:149-155, 1999.

CHO cells expressing human Kv1.5 are cultured as described above, then harvested with trypsin-EDTA and washed with medium.
1. 40,000 cells per well are seeded in a 96-well cell culture plate (assay plate) and the cells are allowed to grow for 48 hours at 37° C.
2. The medium is removed and 200 μl of Rb Load Buffer (Aurora Biomed, Vancouver, BC) is added for 3 hours at 37° C. under 5% CO$_2$.
3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1−(A−B)/(C−B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppressant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:
1. A compound of the structure:

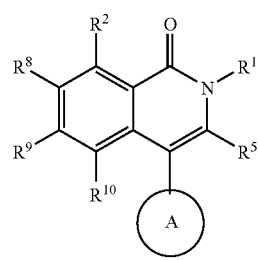

I or a pharmaceutically acceptable salt, crystal form, or hydrate, wherein:
  A is
    a) an aryl ring, wherein any stable aryl ring atom is independently unsubstituted or substituted with
      1) halogen,
      2) $NO_2$,
      3) CN,
      4) $CR^{46}=C(R^{47}R^{48})_2$,
      5) $C\equiv CR^{46}$,
      6) $(CR^iR^j)_rOR^{46}$,
      7) $(CR^iR^j)_rN(R^{46}R^{47})$,
      8) $(CR^iR^j)_rC(O)R^{46}$,
      9) $(CR^iR^j)_rC(O)OR^{46}$,
      10) $(CR^iR^j)_rR^{46}$,
      11) $(CR^iR^j)_rS(O)_{0-2}R^{61}$,
      12) $(CR^iR^j)_rS(O)_{0-2}N(R^{46}R^{47})$,
      13) $OS(O)_{0-2}R^{61}$,
      14) $N(R^{46})C(O)R^{47}$,
      15) $N(R^{46})S(O)_{0-2}R^{61}$,
      16) $(CR^iR^j)_rN(R^{46})R^{61}$,
      17) $(CR^iR^j)_rN(R^{46})R^{61}OR^{47}$, 18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo, or b) a heteroaryl ring selected from the group consisting of
  a 5-membered unsaturated monocyclic ring with 1, 2, 3 or 4 heteroatom ring atoms selected from the group consisting or N, O or S,
  a 6-membered unsaturated monocyclic ring with 1, 2, 3 or 4 heteroatom ring atoms selected from the group consisting N, O and S, and
  a 9- or 10-membered unsaturated bicyclic ring with 1, 2, 3 or 4 heteroatom ring atoms selected from the group consisting or N, O or S;
  wherein any stable S heteroaryl ring atom is unsubstituted or mono- or di-substituted with oxo, and any stable C or N heteroaryl ring atom is independently unsubstituted or substituted with
  1) halogen,
  2) $NO_2$,
  3) CN,
  4) $CR^{46}=C(R^{47}R^{48})_2$,
  5) $C\equiv CR^{46}$,
  6) $(CR^iR^j)_rOR^{46}$,
  7) $(CR^iR^j)_rN(R^{46}R^{47})$,
  8) $(CR^iR^j)_rC(O)R^{46}$,
  9) $(CR^iR^j)_rC(O)OR^{46}$,
  10) $(CR^iR^j)_rR^{46}$,
  11) $(CR^iR^j)_rS(O)_{0-2}R^{61}$,
  12) $(CR^iR^j)_rS(O)_{0-2}N(R^{46}R^{47})$,
  13) $OS(O)_{0-2}R^{61}$,
  14) $N(R^{46})C(O)R^{47}$,
  15) $N(R^{46})S(O)_{0-2}R^{61}$,
  16) $(CR^iR^j)_rN(R^{46})R^{61}$,
  17) $(CR^iR^j)_rN(R^{46})R^{61}OR^{47}$,
  18) $(CR^iR^j)_rN(R^{46})(CR^kR^l)_sC(O)N(R^{47}R^{48})$,
  19) $N(R^{46})(CR^iR^j)_rR^{61}$,
  20) $N(R^{46})(CR^iR^j)_rN(R^{47}R^{48})$,
  21) $(CR^iR^j)_rC(O)N(R^{47}R^{48})$, or
  22) oxo;

$R^1$ and $R^5$ together with the atoms to which they are attached, form a ring selected from the group of structures consisting of

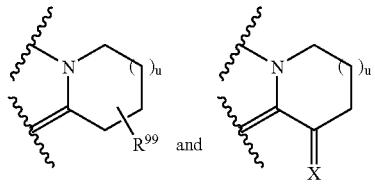

where u is 0 or 1, $R^{99}$ is hydrogen or —OH, and X is O or =NOH;

$R^2$, $R^8$, $R^9$ and $R^{10}$ are independently selected from:
1) hydrogen,
2) halogen,
3) $NO_2$,
4) CN,
5) $CR^{43}=C(R^{44}R^{45})$,
6) $C\equiv CR^{43}$,
7) $(CR^eR^f)OR^{43}$,
8) $(CR^eR^f)N(R^{43}R^{44})$,
9) $(CR^eR^f)C(O)R^{43}$,
10) $(CR^eR^f)C(O)OR^{43}$,
11) $(CR^eR^f)R^{43}$,
12) $(CR^eR^f)PS(O)_{0-2}R^{60}$,
13) $(CR^eR^f)PS(O)_{0-2}N(R^{43}R^{44})$,
14) $OS(O)_{0-2}R^{60}$,
15) $N(R^{43})C(O)R^{44}$,
16) $N(R^{43})S(O)_{0-2}R^{60}$,
17) $(CR^eR^f)N(R^{43})R^{60}$,
18) $(CR^eR^f)N(R^{43})R^{60}OR^{44}$,
19) $(CR^eR^f)_pN(R^{43})(CR^gR^h)_qC(O)N(R^{44}R^{45})$,
20) $N(R^{43})(CR^eR^f)R^{60}$,
21) $N(R^{43})(CR^eR^f)N(R^{44}R^{45})$, and
22) $(CR^eR^f)_pC(O)N(R^{43}R^{44})$, or $R^2$ and $R^8$ are independently as defined above, and $R^9$ and $R^{10}$, together with the atoms to which they are attached, form the ring

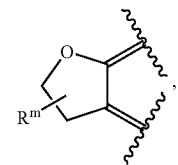

where $R^m$ is $C_{1-6}$alkyl;

$R^a$, $R^b$, $R^c$, $R^d$, $R^e$, $R^f$, $R^g$, $R^h$, $R^i$, $R^j$, $R^k$, and $R^l$ are independently selected from the group consisting of:
1) hydrogen,
2) $C_1$-$C_6$ alkyl,
3) halogen,
4) aryl,
5) $R^{80}$,
6) $C_3$-$C_{10}$ cycloalkyl, and
7) $OR^4$,
said alkyl, aryl, and cycloalkyl being unsubstituted, monosubstituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$ and $R^{17}$;

$R^4$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{53}$ and are independently selected from the group consisting of
1) hydrogen,
2) $C_1$-$C_6$ alkyl,
3) $C_3$-$C_{10}$ cycloalkyl,
4) aryl,
5) $R^{81}$,
6) $CF_3$,
7) $C_2$-$C_6$ alkenyl, and
8) $C_2$-$C_6$ alkynyl,
said alkyl, aryl, and cycloalkyl is unsubstituted, monosubstituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;

$R^6$, $R^{60}$, $R^{61}$, $R^{62}$ and $R^{63}$ are independently selected from the group consisting of
1) $C_1$-$C_6$ alkyl,
2) aryl,
3) $R^{83}$, and
4) $C_3$-$C_{10}$ cycloalkyl;
said alkyl, aryl, and cycloalkyl is unsubstituted, monosubstituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, and are independently selected from the group consisting of
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$, —
10) $C(O)R^{51}$,
11) CN,
12) $C(O)N(R^{51}R^{52})$,
13) $N(R^{51})C(O)R^{52}$,
14) $S(O)_{0-2}R^{63}$,
15) $NO_2$, and
16) $N(R^{51}R^{52})$;

$R^{80}$, $R^{81}$, $R^{82}$, $R^{83}$ and $R^{84}$ are independently selected from a group of unsubstituted or substituted hetrocyclic rings consisting of a 4-6 membered unsaturated or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S; and n, p, q, r, and s are independently 1, 2, 3, 4, 5 or 6;

provided that when $R^9$ is $OCH_3$, $R^1$ is $CH_3$ and $R^5$ is $C(CH_3)_3$, then A is substituted, when $R^9$ is hydrogen, $R^1$ is $CH_3$, and $R^5$ is hydrogen, then A is substituted, when $R^9$ is hydrogen, $R^1$ is $CH_3$, and $R^5$ is $C(CH_3)_3$, then A is substituted, provided the subsistent is not $CH_3$, and when $R^9$ is $OCH_3$, $R^1$ is $CH_3$, $R^5$ is $CH_3$, then A is substituted wherein the compound, or a pharmaceutically acceptable salt thereof, is 11-(3-fluorophenyl)-9-methoxy-3,4-dihydro-2H-pyrido[1,2-b]isoquinoline-1,6-dione.

2. A method of treating a condition in a mammal, the treatment of which is effected or facilitated by $K_v1.5$ inhibition, which comprises administering a compound of claim 1 in an amount that is effective at inhibiting $K_v1.5$ wherein the condition is cardiac arrhythmia.

3. A method of claim 2, wherein the cardiac arrhythmia is selected from the group consisting of atrial flutter, atrial arrhythmia and supraventricular tachycardia.

4. A method of claim 3, wherein the cardiac arrhythmia is atrial fibrillation.

5. A method of treating cardiac arrhythmia comprising administering a compound of claim 1 with a compound selected from one of the classes of compounds consisting of antiarrhythmic agents having $K_v1.5$ blocking activities, ACE inhibitors, angiotensin II antagonists, cardiac glycosides, L-type calcium channel blockers, T-type calcium channel blockers, selective and nonselective beta blockers, endothelin antagonists, thrombin inhibitors, aspirin, nonselective NSAIDs, warfarin, factor Xa inhibitors, low molecular weight heparin, unfractionated heparin, clopidogrel, ticlopidine, IIb/IIIa receptor antagonists, 5HT receptor antagonists, integrin receptor antagonists, thromboxane receptor antagonists, TAFI inhibitors and P2T receptor antagonists.

6. A method for treating tachycardia in a patient which comprises treating the patient with an antitachycardia device in combination with a compound of claim 1.

7. A pharmaceutical formulation comprising a pharmaceutically acceptable carrier and the compound claim 1 or a pharmaceutically acceptable crystal form or hydrate thereof.

8. A pharmaceutical composition made by combining the compound of claim 1 and a pharmaceutically acceptable carrier.

* * * * *